United States Patent [19]
Ikeda et al.

[11] Patent Number: 5,545,759
[45] Date of Patent: *Aug. 13, 1996

[54] METHOD OF PRODUCING TRIS(PENTAFLUOROPHENYL)BORANE USING PENTAFLUOROPHENYL ALKALI METAL SALT PREPARED FROM PENTAFLUOROBENZENE

[75] Inventors: Yoshihiko Ikeda, Shinnanyo; Takeo Yamane, Ogori-machi; Eiichi Kaji; Kenji Ishimaru, both of Shinnanyo, all of Japan

[73] Assignee: Tosoh Akzo Corporation, Tokyo, Japan

[*] Notice: The term of this patent shall not extend beyond the expiration date of Pat. No. 5,493,056.

[21] Appl. No.: 379,026

[22] Filed: Jan. 27, 1995

Related U.S. Application Data

[63] Continuation of Ser. No. 171,617, Dec. 22, 1993, abandoned.

[30] Foreign Application Priority Data

Dec. 28, 1992 [JP] Japan ................... 4-361476

[51] Int. Cl.[6] ......................... C07F 5/02
[52] U.S. Cl. ............................... 568/6
[58] Field of Search ................... 568/6

[56] References Cited

U.S. PATENT DOCUMENTS 3,311,662  3/1967  Washburn et al. .

FOREIGN PATENT DOCUMENTS 0505973  9/1992  European Pat. Off. .

OTHER PUBLICATIONS

Chemical Abstracts, vol. 93, No. 19, Nov. 10, 1980, AN 185318w, S. S. Dua, et al., p. 572, "Reactions of Hydrofluorobenzenes With Some Organolithium Reagents, Methyllithium, N–Butyllithium and Tert–Butyllithium".

Chemical Abstracts, vol. 59, No. 8, Oct. 14, 1963, AN 8771b, A. G. Massey, et al., "Tris(Pentafluorophenyl)Boron".

Chemical Abstracts, vol. 100, No. 17, Apr. 23, 1984, AN 139179s, Hiroshi Kobayashi, et al., "Synthesis of Trifluoromethylated Tetraphenylborates and the Solvent–Extraction Properties of Their Ion–Associates With Alkali–Metal Ions. Application of Tetraarylborates to Separation Analysis of Univalent Cations", p. 660.

The Journal of Organic Chemistry, vol. 29, 1964, pp. 2385–2389, Robert J. Harper, Jr., et al. "Reactions of Organometallics With Fluoroaromatac Compounds".

*Primary Examiner*—Robert W. Ramsuer
*Assistant Examiner*—John Peabody
*Attorney, Agent, or Firm*—Oblon, Spivak, McClelland, Maier & Neustadt, P.C.

[57] ABSTRACT

The invention relates to a production method, wherein, with 1 equivalent of pentafluorobenzene of the formula $C_6HF_5M$, 0.5 to 1.5 equivalents of an organometallic compound of the formula RM, wherein R is a hydrocarbon group of 1 to 10 carbon atoms and m is an alkali metal ion, are reacted at $-120°$ to $80°$ C. in an ether type solvent, a hydrocarbon type solvent or a mixed solvent of the ether type solvent with the hydrocarbon type solvent to generate a pentafluorophenyl alkali metal salt of the formula $C_6F_5M$. Next, 1 equivalent of a boron compound of the formula $BX_3$, where X is halogen, OR or NR'R" is reacted with 2.1 to 3.9 equivalents of a pentafluorophenyl alkali metal salt of the formula $C_6F_5M$ within a temperature range from $-120°$ to $80°$ C. to produce tris(pentafluorophenyl)borane of the formula $(C_6F_5)_3B$ or a complex of tris(pentafluorophenyl)borane coordinated with the ether type solvent.

5 Claims, No Drawings

METHOD OF PRODUCING TRIS(PENTAFLUOROPHENYL)BORANE USING PENTAFLUOROPHENYL ALKALI METAL SALT PREPARED FROM PENTAFLUOROBENZENE

This application is a continuation of application Ser. No. 08/171,617, filed on Dec. 22, 1993, now abandoned.

BACKGROUND OF THE INVENTION

The present invention relates to a novel production method of tris(pentafluorophenyl)borane using pentafluorobenzene as a raw material. Tris(pentafluorophenyl)borane obtainable according to the invention is a very useful substance as a cocatalyst for the cationic complex polymerization or an intermediate of N,N-dimethylanilinium tetrakis(pentafluorophenyl)borate etc., which is useful similarly as a cocatalyst for the cationic complex polymerization.

In recent years, scientific literatures or patents dealing with the polymerization reaction using these compounds and organometallic complexes have increased remarkably. For example, J. Am. Chem. Soc., 113, 3626 (1991), Macromol. Chem. Rapid Commun., 2, p. p. 663–667 (1991) and the like are available. However, for the production of tris(pentafluorophenyl)borane, relatively expensive pentafluorobromobenzene has been used conventionally as a starting substance for the source of pentafluorophenyl group.

The method was that pentafluorobromobenzene was submitted to the bromine-metal exchange reaction at low temperature of −70° C. using organometallic compounds such as butyllithium to generate pentafluorophenyllithium (J. Org. Chem., 29, 2385 (1964), J. Org. Chem., 31, 4229 (1966) and Synthesis of Fluoroorganic Compounds, p. 190, Springer-Verlag (1985)), which was then reacted with boron trichloride, boron trifluoride, or the like as a starting raw material of the source of boron, or that pentafluorobromobenzene was reacted with magnesium to generate a Grignard reagent like pentafluorophenylmagnesium bromide (J. Chem. Soc., 166 (1959), Z. Naturforschg., 20b, 5 (1965), Synthesis of Fluoroorganic Compounds, p. 141, Springer-Verlag (1985), which was then reacted with boron trichloride similarly as a starting raw material of the source of boron, thereby performing the production of tris(pentafluorophenyl)borane (J. Organometallic Chem., 2, 245–250 (1964).

Pentafluorobromobenzene is obtained by brominating pentafluorobenzene. If it is possible to directly produce tris(pentafluorophenyl)borane from pentafluorobenzene, then the production processes can be reduced by one process, leading to easy availability and also decreased price of a starting raw material.

In view of the said situation, the inventors investigated extensively on a synthetic method without using relatively expensive bromopentafluorobenzene as a starting raw material by changing the use of bromopentafluorobenzene to that of pentafluorobenzene as a starting substance for the production of tris(pentafluorophenyl)borane and eliminating the brominating process of pentafluorobenzene, leading to the invention.

SUMMARY OF THE INVENTION

The gist of the invention lies in a process for producing tris(pentafluorophenyl)borane by reacting 1 equivalent of pentafluorobenzene of the formula $$C_6HF_5 \qquad (I),$$

with 0.5 to 1.5 equivalents of an organometallic compound of the formula $$RM \qquad (II),$$

wherein M is an alkali metal ion, and R denotes a hydrocarbon group of 1 to 10 carbon atoms wherein said carbon atoms may contain functional groups having no influence on the reaction, at a reaction temperature of −120° to 80° C. in an ether type solvent, a hydrocarbon type solvent or a mixed solvent of the ether type solvent with the hydrocarbon type solvent, to generate a pentafluorophenyl alkali metal salt of the formula $$C_6F_5M \qquad (III),$$

wherein M denotes an alkali metal ion. Then, 1 equivalent of a borane compound of the formula $$BX_3 \qquad (IV),$$

wherein X is selected from the group consisting of a halogen atom, OR wherein R is as previously defined, or NR'R" wherein R' and R" each denote hydrocarbon groups having 1 to 20 carbon atoms which may contain functional groups having no influence on the reaction, and R' and R" may link one another to form a ring; or a 1:1 complex of said $BX_3$ compound with an ether solvent, is reacted with 2.1 to 3.9 equivalents of an alkali metal salt of the formula, $$C_6F_5M \qquad (III),$$

wherein M denotes an alkali metal ion at a temperature of from −120° to 80° C. to produce tris(pentafluorophenyl)borane of the formula, $$(C_6F_5)_3B \qquad (VII),$$

or a complex of said tris(pentafluorophenyl)borane coordinated with the ether type solvent.

DETAILED DESCRIPTION OF THE INVENTION

In following, the invention will be illustrated concretely.

The ether type solvents referred to so in the specification indicate diethyl ether, dipropyl ether, diisopropyl ether, dibutyl ether, diisoamyl ether, etc.

Next, the hydrocarbon type solvents referred to so in the invention indicate saturated hydrocarbons such as pentane, isopentane, hexane, cyclohexane, heptane, octane, nonane, decane, undecane, dodecane, tridecane, tetradecane, pentadecane, hexadecane and n-paraffin and petroleum ether, aromatic hydrocarbons such as benzene, toluene, o-xylene, m-xylene, p-xylene, 1,2,3-trimethylbenzene, 1,2,4-trimethylbenzene, 1,2,5-trimethylbenzene, 1,3,5-trimethylbenzene, ethylbenzene, propylbenzene and butylbenzene, and mixtures thereof.

Next, the functional groups having no influence on the reaction in formula [II] referred to so in the specification indicate methyl group, ethyl group, propyl group, isopropyl group, propenyl group, 2-isopropenyl group, allyl group, butyl group, sec-butyl group, tert-butyl group, isobutyl group, pentyl group, sec-pentyl group, tert-pentyl group, neo-pentyl group, isopentyl group, sec-isopentyl group, hexyl group, sec-hexyl group, isohexyl group, sec-isohexyl group, cyclohexyl group, phenyl group, benzyl group, o-tolyl group, m-tolyl group, p-tolyl group, methoxymethyl group, methylthiomethyl group, 2-dimethylaminoethyl group, o-anisyl group, m-anisyl group, p-anisyl group, trimethylsilylmethyl group, etc. and examples of organometallic compounds represented by the formula II include methyllithium, ethyllithium, propyllithium, isopropyllithium, butyllithium, isobutyllithium, sec-butyllithium, tert-butyllithium, pentyllithium, isopentyllithium, sec-pentyllithium, tert-pentyllithium, sec-isopentyllithium, hyxyllithium, isohexyllithium, sec-hexyllithium, cyclohexyllithium, phenyllithium, o-tolyllithium, m-tolyllithium, p-tolyllithium, trimethylsilylmethyllithium, phenylsodium, o-tolylsodium, m-tolylsodium, p-tolylsodium, butyllithium/potassium-tert-butoxide, butyllithium/sodium-tert-butoxide, etc., and isopropyllithium, sec-butyllithium, tert-butyllithium, sec-pentyllithium, tert-pentyllithium, sec-isopentyllithium, sec-hexyllithium, cyclohexyllithium, etc. which are strong in basicity and hard to influence on the reaction, are preferable.

As the examples of boron compounds represented by the formula [IV] referred to so in the specification, boron trifluoride, boron trichloride, boron tribromide, boron triiodide, trimethylboric acid, triethylboric acid, tripropylboric acid, triisopropylboric acid, tributylboric acid, trimethyleneborate, tris(dimethylamino)borate, tris(diethylamino)borate, tripyrrolidinoborate, tripiperidinoborate, trimorpholinoborate, etc. are mentioned. In addition, the complexes such as boron trifluoride-diethyl ether complex, boron trifluoride-dibutyl ether complex, boron trifluoride-dimethyl sulfide complex, boron trichloride-diethyl ether complex and boron trichloride-dibutyl ether complex are also included in this category.

The concrete production method will be illustrated below in sequence.

Pentafluorobenzene represented by the formula [I] is dissolved into an ether type solvent, a hydrocarbon type solvent or a mixed solvent thereof. With this solution, 0.5 to 1.5 equivalents of organometallic compound represented by the formula [II] per 1 equivalent of pentafluorobenzene are reacted within a range from −120° to 80° C.

In this reaction, when generating pentafluorophenyl alkali metal salt represented by the formula [III], if organometallic compound represented by the formula [II] is too less than pentafluorobenzene represented by the formula [I], then a lot of unreacted pentafluorobenzene comes to remain, and, if excess amount of organometallic compound is used, then there is a fear of the halogen-metal exchange reaction with also fluorine of pentafluorophenyl metal salt produced and represented by the formula [III]. Hence it is preferable to use 0.8 to 1.20 equivalents of organometallic compound represented by the formula [II].

If the reaction temperature is much lower than −80° C., the reaction proceeds extremely slowly, while if it is much higher than 0° C., side reactions proceed extremely rapidly, thus coming to very low yield in both cases. Hence it is desirable to conduct the reaction in a range of −80° to 0° C. The reaction mixture is allowed to react for 5 to 120 minutes at the same temperature, thereby pentafluorophenyl alkali metal salt represented by the formula [III] is prepared. Pentafluorophenyl alkali metal salt produced herein and represented by the formula [III] is $C_6H_5Li$, $C_6H_5Na$ or $C_6H_5K$.

Although the use level of pentafluorophenyl alkali metal salt is 3 equivalents as a theoretical amount when using the boron compound represented by the formula [IV] for the reaction, the decrease in the yield of tris(pentafluorophenyl)borane becomes remarkable in the case of under 2.1 equivalents shown here, and the production of tetrakis(pentafluorophenyl)borate derivatives becomes remarkable leading to the decreased yield of tris(pentafluorophenyl)borane in the case of exceeding 3.9 equivalents, hence use of 2.1 to 3.9 equivalents is desirable.

As for the mixing temperature of pentafluorophenyl alkali metal salt with the boron compound, the reaction proceeds extremely slowly at a temperature lower than −80° C., hence a temperature higher than this is desirable, and, if it is higher than 0° C., side reactions proceed extremely rapidly, thus coming to very low yield in both cases. Hence a temperature lower than this is desirable.

Also, if the reaction temperature is lower than −80° C., then the reaction proceeds extremely slowly, and, if it is higher than 0° C., then the unreacted pentafluorophenyl alkali metal salt decomposes, hence reacting at −80° to 0° C. is desirable.

By reacting the reaction mixture for 0.5 to 50 hours within a range from −80° to 80° C., tris(pentafluorophenyl)borane represented by the formula [VII] or a complex of tris(pentafluorophenyl)borane coordinated with the ether type solvent can be produced. At that time, preferably, the reaction temperature is further raised within a range from 20° to 80° C. and the reaction is continued for 0.5 to 50 hours to complete the reaction.

The ether type solvent coordinated to tris(pentafluorophenyl)borane can be removed by direct removing method or indirect removing method. The direct removing method referred to so here is a method wherein the complex represented by the formula [VII] is evaporated and sublimated at 30° to 200° C. and below 10 Torr, desirably below 1 Torr after distilled off the solvent.

Next, the indirect removing method referred to so here includes two methods; (1) a method wherein 1 equivalent or more of alkylaluminum to the solvent, which is coordinated to tris(pentafluorophenyl)borane, is reacted to coordinate that solvent to the used alkylaluminum, thereby removing the solvent and (2) a method wherein hydrocarbon type solvent with higher boiling point than that of coordinated solvent is mixed and this hydrocarbon type solvent is distilled off, thereby removing the coordinated solvent azeotropically.

When removing the coordinated solvent by the method (2), by heating to 60° to 200° C., preferably not lower than 100° C., using hydrocarbon type solvent, it becomes possible to remove the ether type solvent. Hence, the hydrocarbon type solvent to be used for azeotropic removal is preferable to have a boiling point of 100° to 200° C. With the saturated hydrocarbons, the solubility of tris(pentafluorophenyl)borane produced and represented by the formula [VII] is low, hence, when purifying it by crystallization after removing the coordinated solvent, a use of octane, nonane, decane, undecane, dedecane, tridecane, mixtures thereof, etc. is desirable above all. Inversely, with the aromatic hydrocarbons, the solubility of tris(pentafluorophenyl)borane or a complex of tris(pentafluorophenyl)borane coordinated with solvent produced is relatively high, hence, when using as a solution, a use of toluene, o-xylene, m-xylene, p-xylene, ethylbenzene, propylbenzene, etc. is desirable.

The invention can provide a method of more inexpensively producing tris(pentafluorophenyl)borane or a complex of tris(pentafluorophenyl)borane coordinated with the ether type solvent, being very important compound as a cocatalyst for the cationic complex polymerization, with production processes shortened by one process by changing the starting raw material from expensive bromopentafluorobenzene to pentafluorobenzene, and yet has a tremendous industrial worth in the point of being possible to fully bring out the ability as a cocatalyst by removing the coordinated ether type solvent.

In following, the invention will be illustrated in detail using the examples, but the invention is not confined to the examples below.

EXAMPLE 1

After a solution of pentafluorobenzene (11.0 g, 65.2 mmol) and diethyl ether (100 ml) was cooled to −40° C., a 20 wt. % butyllithium/hexane solution (19.0 g, 59.3 mmol) was added and the mixture was stirred for 1 hour at −30° to −40° C. Thereafter, 1 mol/L boron trichloride/hexane solution (19.5 ml, 19.5 mmol) was added at −40° C. and the temperature was raised to room temperature over 2 hours. After stirring overnight at room temperature, toluene (100 ml) was added and, after distilled off diethyl ether and hexane under heat, toluene was also distilled off further under heat to an extent of recovering about 30% of the added amount. The diethyl ether complex of tris(pentafluorophenyl)borane obtained by removing toluene to bone-dry after filtered off precipitated lithium chloride was further mixed with toluene refluxed under heat and toluene was removed to obtain crude tris(pentafluorophenyl)borane in 55.8% yield. When determining the purity of crude tris(pentafluorophenyl)borane thus obtained by means of $^{19}F$ NMR, it showed 95%.

EXAMPLE 2

After a solution of pentafluorobenzene (10.0 g, 59.5 mmol) and diisopropyl ether (100 ml) was cooled to −40° C., a 24 wt. % tert-butyllithium/pentane solution (15.9 g, 59.5 mmol) was added and the mixture was stirred for 0.5 hours at −30° to −40° C. Thereafter, 1 mol/L boron trichloride/ hexane solution, (19.0 ml, 19.0 mmol) was added at −40° C. and the temperature was raised to room temperature over 2 hours. After stirring overnight at room temperature, octane (100 ml) was added and, after distilled off diisopropyl ether, hexane and pentane under heat, octane was also distilled off further under heat to an extent of recovering about 30% of the added amount. After filtered off precipitated lithium chloride, octane was removed to bone-dry to obtain crude tris(pentafluorophenyl)borane in 61.3% yield. When determining the purity of crude tris(pentafluorophenyl)borane thus obtained by means of $^{19}F$ NMR, it showed 97%. When sublimating crude tris(pentafluorophenyl)borane under vacuum, tris(pentafluorophenyl)borane was obtained in 40.1% yield.

EXAMPLE 3

After a solution of pentafluorobenzene (10.0 g, 59.5 mmol) and diethyl ether (100 ml) was cooled to −40° C., a 24 wt. % tert-butyllithium/pentane solution (15.8 g, 59.1 mmol) was added and the mixture was stirred for 0.5 hours at −30° to −40° C. Thereafter, trimethyl borate (2.00 g, 19.2 mmol) was added at −40° C. and the temperature was raised to room temperature over 2 hours. After stirring overnight at room temperature, octane (100 ml) was added and, after distilled off diethyl ether and pentane under heat, octane was also distilled off further under heat to an extent of recovering about 30% of the added amount. After filtered off precipitated lithium methoxide, octane was removed to bone-dry to obtain tris(pentafluorophenyl)borane in 45% yield.

EXAMPLE 4

After a solution of pentafluorobenzene (10.0 g, 59.5 mmol) and dibutyl ether (100 ml) was cooled to −40° C., a 15 wt. % butylsodium/hexane solution was added and the mixture was stirred for 1 hour at −30° to −40° C. Thereafter, boron trifluoride-diethyl ether complex (2.73 g, 19.2 mmol) was added at −40° C. and the temperature was raised to room temperature over 2 hours. After stirring overnight at room temperature, decane (100 ml) was added and, after distilled off diethyl ether and hexane under heat, decane was also distilled off further under heat to an extent of recovering about 30% of the added amount. After filtered off precipitated sodium fluoride, decane was removed to bone-dry to obtain tris(pentafluorophenyl)borane in 52% yield.

EXAMPLE 5

After a solution of pentafluorobenzene (10.0 g, 59.5 mmol) and diethyl ether (100 ml) was cooled to −40° C., a 24 wt. % sec-butyllithium/hexane solution (15.8 g, 59.1 mmol) was added and the mixture was stirred for 0.5 hours at −30° to −40° C. Therefor, 1 mol/L hexane solution (19.2 mL, 19.2 mmol) of boron tribromide was added at −40° C. and the temperature was raised to room temperature over 2 hours. After stirring overnight at room temperature, octane (100 ml) was added and, after distilled off diethyl ether and hexane under heat, octane was also distilled off further under heat to an extent of recovering about 30% of the added amount. After filtered off precipitated lithium bromide, the octane solution of tris(pentafluorophenyl)borane was cooled to 0° C. to deposit white crystals. When drying under an atmosphere of nitrogen after the filtration, tris(pentafluorophenyl)borane was obtained in 49.2% yield. When determining the purity of tris(pentafluorophenyl)borane thus obtained by means of $^{19}F$ NMR, it showed 98 wt. % or higher.

What is claimed is:

1. A process for preparing tris(pentafluorophenyl)borane represented by the formula $$(C_6F_5)_3B \qquad (VII),$$

or a complex of tris(pentafluorophenyl)borane coordinated with an ether type solvent, selected from the group consisting of diethyl ether, dipropyl ether, diisopropyl ether, dibutyl ether and diisoamyl ether comprising reacting 1 equivalent of pentafluorobenzene of the formula $$C_6HF_5 \qquad (I),$$

and 0.5 to 1.5 equivalents of an organometallic compound of the formula $$RM \qquad (II)$$

wherein M denotes an alkali metal ion, R denotes a hydrocarbon group with carbon atoms of 1 to 10 and the said hydrocarbon group may contain functional groups having no influence on the reaction, at a temperature range from −120° to 80° C. in an ether type solvent, a hydrocarbon type solvent or a mixed solvent containing both the ether type solvent and the hydrocarbon type solvent to generate a pentafluorophenyl alkali metal salt of the formula $$C_6F_5M \qquad (III)$$

wherein M denotes an alkali metal ion; then reacting 2.1 to 3.9 equivalents of an alkali metal salt of the formula III at a temperature of from −120° to 80° C. with 1 equivalent of a boron compound or a 1:1 complex of a boron compound with an ether type solvent, said boron compound being of the formula $$BX_3 \quad (IV)$$

wherein X denotes a halogen atom, a substituent represented by a following general formula $$OR \quad (V)$$

wherein R denotes a hydrocarbon group with carbon atoms of 1 to 10 and said hydrocarbon may contain functional groups having no influence on the reaction, or a substituent represented by the formula $$NR'R'' \quad (VI)$$

wherein R' and R'' each denote a hydrocarbon group have 1 to 20 carbon atoms, or hydrocarbon groups of 1 to 20 carbon atoms substituted by functional groups having no influence on the reaction, or R' and R'' link one another to form a ring structure.

2. The process of claim 1, wherein said reaction between said organometallic compound of the formula RM and said pentafluorobenzene is carried out at a temperature in the range from −40° to 80° C.

3. The process of claim 1, wherein the solvent is diethyl ether.

4. The process of claim 2, wherein said solvent is diethyl ether.

5. The process of claim 1, wherein said organometallic compound of the formula RM and said pentafluorobenzene are mixed at a temperature in the range −30° to −40° C., and said boron compound is added to said mixture at −40° C. and the reaction is accomplished by raising the temperature to room temperature and stirring at room temperature.

* * * * *